United States Patent [19]
Iida et al.

[11] Patent Number: 5,354,675
[45] Date of Patent: Oct. 11, 1994

[54] C-TERMINAL AMIDATING ENZYME COMPOSITION, PROCESS FOR PREPARING, AND USE OF THE SAME

[75] Inventors: Toshii Iida; Yuka Fuse; Masahiro Tajima; Mitsuo Yanagi, all of Yokohama; Hiroshi Okamoto, Sendai, all of Japan

[73] Assignee: Shiseido Company Ltd., Japan

[21] Appl. No.: 459,829

[22] PCT Filed: May 25, 1989

[86] PCT No.: PCT/JP89/00521

§ 371 Date: Jan. 29, 1990

§ 102(e) Date: Jan. 29, 1990

[87] PCT Pub. No.: WO89/12096

PCT Pub. Date: Dec. 14, 1989

[30] Foreign Application Priority Data

May 30, 1988 [JP] Japan ............................ 63-130187
Apr. 21, 1989 [JP] Japan ............................ 1-99960

[51] Int. Cl.$^5$ .................. C12P 21/00; C12N 9/00; C12N 9/02
[52] U.S. Cl. .................. 435/189; 435/183; 435/68.1
[58] Field of Search ............ 435/189, 68.1, 183

[56] References Cited

FOREIGN PATENT DOCUMENTS 0333399 9/1989 European Pat. Off. .
8701729 3/1987 World Int. Prop. O. .......... 435/68.1

OTHER PUBLICATIONS

Murthy et al, (1987) *Mol. Endrocriol.*, 1(4), 290–299.
Eipper et al, (1987) *Mol. Endocrinol.*, 1(11), 777–790.
Pesce et al, (1967) *J. Biol. Chem.*, 242(9), 2151–2167.
Sakata et al. (1986) *Biochem Biophys. Res. Comm.*, 140(1), 230–236.
Stoffers et al. (1989) *Proc. Nat. Acad. Sci. USA*, 86, 735–739.
J. Biol. Chem., vol. 261, No. 4, (1986), A. S. N. Murthy, et al. [Purification and Characterization of Peptidylglycine α–Amidating Monooxygenase from Bovine Neurointermediate Pituitary] pp. 1815–1822.
Endocrinology, vol. 118, No. 6, (1986), J. S. Kizer, et al [Purification and Characterization of a Peptidyl Glycine Monooxygenase from Porcine Pituitary] pp. 2262–2267.
Endocrinology, vol. 116, No. 6, (1985), B. A. Eipper, et al [Peptidyl–Glycine α–Amidation Activity in Tissues and Serum of the Adult Rat] pp. 2497–2504.
Metabolism, vol. 34, No. 11, (1985), G. S. Wand, et al [Characterization of a Peptide Alpha–Amidation Activity In Human Plasma and Tissues] pp. 1044–1052.
Gastroenterology, vol. 92, No. 5, (1987), T. Azuma, et al [COOH–Terminal Glycine Extended Progastrin(-Gastrin–G) and Peptidyl–Glycine α–Amidating Monooxigenase(PAM)Activity in Rat Serum] p. 1302.

*Primary Examiner*—Irene Marx
*Assistant Examiner*—Jon P. Weber
*Attorney, Agent, or Firm*—Wegner, Cantor, Mueller & Player

[57] ABSTRACT

A C-terminal amidating enzyme composition is disclosed having the ability to amidate the C-terminus of peptides with a C-terminal glycine. The C-terminal amidating enzyme is characterized by having a stable pH range of 5 to 9, metal ions and L-ascorbic acid as cofactors, two active fractions at molecular weights of about 50,000 and about 100,000 as determined from gel filtration, isoelectric points of about 4.5 pH for the active fraction having a molecular weight of about 50,000 and about 6.7 pH for the active fraction having a molecular weight of about 100,000 according to isoelectric point chromatography, and is activated by addition of catalase.

6 Claims, 2 Drawing Sheets

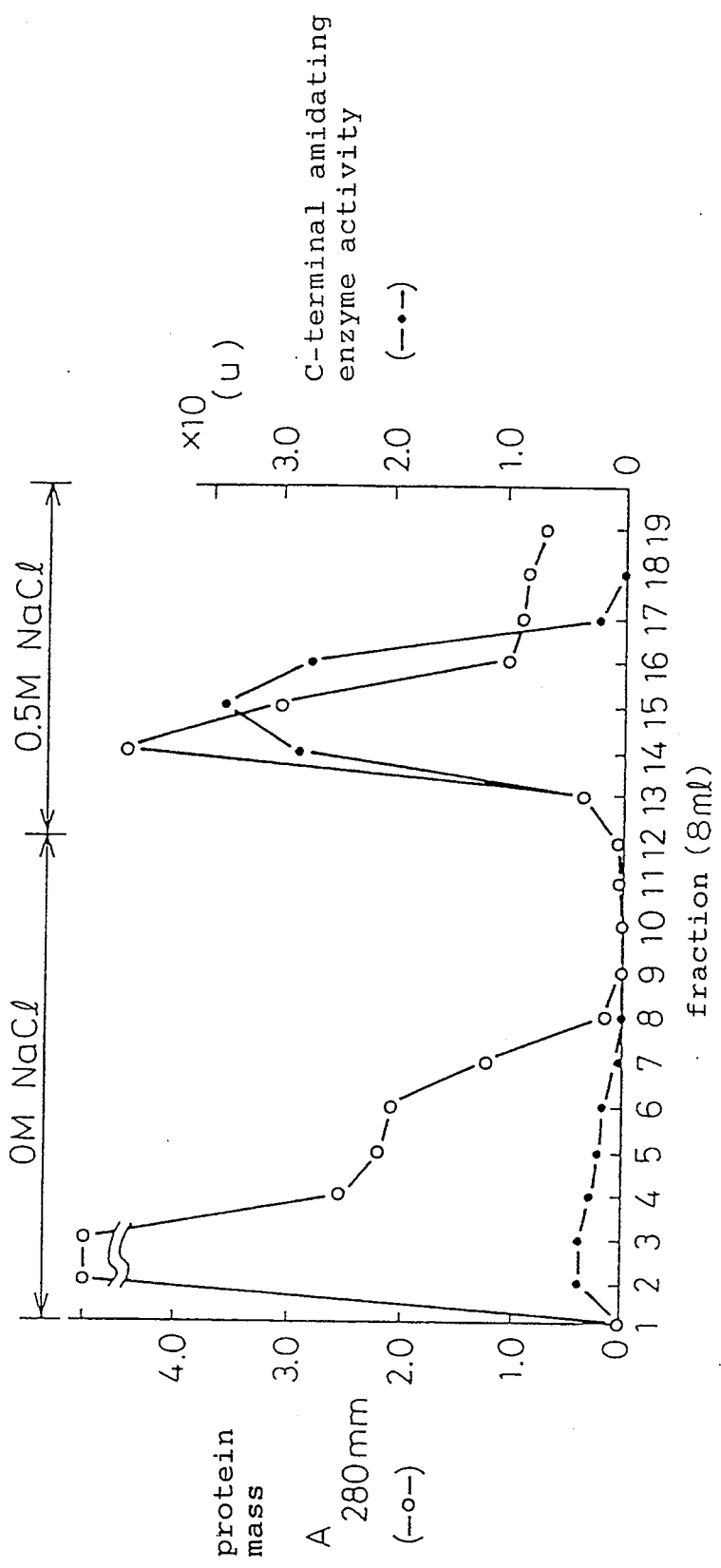

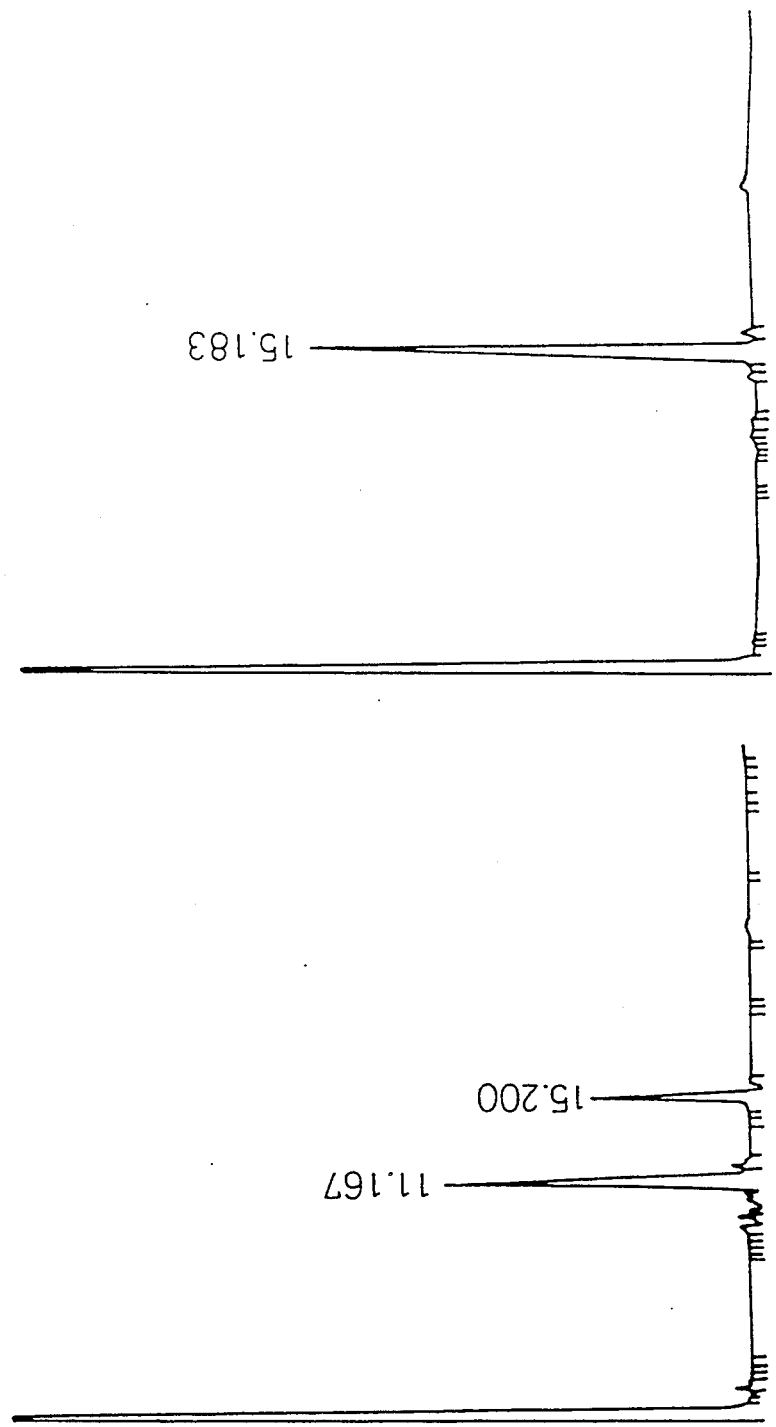

C-TERMINAL AMIDATING ENZYME COMPOSITION, PROCESS FOR PREPARING, AND USE OF THE SAME

TECHNICAL FIELD

This invention relates to a C-terminal amidating enzyme composition derived from serum or plasma, a process for preparing the same and a method of production a peptide amidated at the C-terminal or a derivative thereof utilizing the same.

BACKGROUND ART

Peptides, which exhibit biological activity for the first time when C-terminal is amidated, for example, calcitonin, gastrin, secretin, vasoactive intestinal polypeptide, growth hormone-releasing factor, corticotropin-releasing factor, etc. have been known to be formed from glycine adducts through enzymatic reactions in vivo. Many of these biologically active peptides are useful as pharmaceuticals, and presently calcitonin, secretin, among others, are commercially available as pharmaceuticals.

These peptides have been obtained primarily by separation and purification from living bodies, but the steps are cumbersome and living bodies as sources are obtained only with difficulty. Therefore, the above presently commercially available peptides are very expensive.

Accordingly, in recent years, attempts have been made to produce these biologically active peptides by using a recombinant DNA technique. But according to the recombinant DNA technique using *Escherichia coli*, yeast, *Bacillus subtilis*, and the like as the host, an C-terminal amidation of the peptide produced cannot be effected, which has been an obstacle to producing the above peptide. Accordingly, there is a demand for a technique whereby C-terminal amidation is effected easily and inexpensively in vitro.

The enzyme participating in such amidation is called peptidylglycine-α-amidating monoxygenase (C-terminal amidating enzyme) (EC.1.14.17.3) (Bradbury et al, Nature, 298, 686, 1982: Glembotski et al, J. Biol, Chem., 259, 6385, 1984),and is considered to catalyze the following reaction:

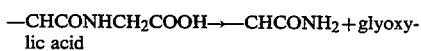
—CHCONHCH$_2$COOH→—CHCONH$_2$+glyoxylic acid

To clarify the amidation mechanism in vivo and amidate the peptide produced by the recombinant technique at the C-terminal in vitro, attempts have been made to purify this enzyme. As examples which have a purified specific activity to 100-fold based source or higher, there have been reported those derived from bovine pituitary gland middle lobe (Murthy et al, J. Biol. Chem., 261, 1815, 1986), porcine pituitary gland (Kizer et al, Endocrinology, 118, 2262, 1986; Bradbury et al, Eur. J. Blochem., 169, 579, 1987), porcine heart atrium (Kojima et al, J. Blochem., 105, 440, 1989), Xenopus body skin (Mizuno et al, Biochem., Biophys. Res. Commun., 137, 984, 1986, rat thyroid gland tumor (Mehta et al, Arch. Biochem., Biophys., 261, 44, 1988). But, except for the method of Kizer et al, the operation is cumbersome, involving 5 to 6 purification steps. Also, according to the method of Kizer et al, there is the step of Sephadex G-100 (produced by Pharmacia) gel filtration, and this takes a long time for elution, and at the same time it is difficult to treat a large amount of the product.

In addition, concerning the existence of the C-terminal amidating enzyme in blood, there are reports of rat (Eipper et al, Endocrinology, 116, 2497, 1985) and human (Wand et al, Metabolism, 34, 1044, 1985), but both have low specific activities and no attempt at purification thereof have been made.

As described above, no purification method capable of simple and bulk treatment of the C-terminal amidating enzyme has been established. Also, no purification has been done from serum and plasma, and no method of producing a peptide amidated at the C-terminal or derivative thereof at low cost and in large which utilizing a C-terminal amidating enzyme in vitro, is known.

DISCLOSURE OF INVENTION

As described above, the C-terminal amidating enzyme exhibits a very interesting action in vivo, and a composition having a constant purity derived from a specific living body organ is known. Nevertheless, the use of these enzyme compositions for practical reactions in vitro, partly because of the difficulty of the availability thereof, is not always satisfactory.

On the other hand, the present inventors studied intensively to find an enzyme composition useful for the above enzyme reaction in vitro, and consequently, surprisingly found that serum or plasma, particularly of horse or porcine, have high enzyme activities, and further, such serum or plasma and enzyme compositions derived from serum or plasma have a catalyzing activity in said enzymatic reaction in vitro, to accomplish the present invention.

Accordingly, this invention provides a C-terminal amidating enzyme composition derived from serum or plasma which acts on a peptide, protein or a derivative thereof with a residue at the C-terminal to participate in the reaction for forming a product amidated at the C-terminal, a process for producing said enzyme composition, and the use of the same.

BRIEF DESCRIPTION OF DRAWINGS

FIG. 1 is a graph showing the elution pattern of the heparin-Sepharose CL-6B column chromatography; and, FIG. 2 is a graph showing the absorption at 214 nm when the reaction of the enzyme sample prepared from horse serum is carried out according to Example 2 with Phe-Gly-Phe-Gly as the substrate by using 10 μl for (1) and 50 μl for (2), and the product is analyzed by HPLC.

BEST MODE OF CARRYING OUT THE INVENTION

[Enzyme Composition]
More specifically, the present invention relates to a C-terminal amidating enzyme composition derived from serum or plasma which acts on a C-terminal glycine adduct represented by the following formula:

X—N—A—CONHCH$_2$COOH  (I)

(wherein A represents a residue other than α-carboxyl group and an α-amino group or imino group derived from naturally occurring α-amino acid, X represents hydrogen atom or a residue of an amino acid derivative which is bonded to N atom through carbonyl group) to participate in the reaction for forming a C-terminal amidated product represented by the following formula:

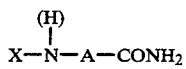
(II)

(wherein A and X have the same meanings as above) and glyoxylic acid, and has a purity which exerts substantially no bad influence on said reaction.

In the formula (I) and (II), the hydrogen atom in the bracket (H) means no hydrogen atom exists when A is derived from an α-amino acid having an α-imino group.

The C-terminal glycine adduct represented by the formula (I) of the present invention, namely the substrate of the enzyme composition of the present invention, may include generally compounds derived from amino acid derivatives wherein the

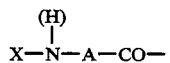

moiety in the above formula is natural or synthetic, particularly, peptides or proteins, with glycine being peptide bonded to the C-terminal amino acid residue thereof [represented by —N(H)—A—CO—]. As the C-terminal amino acid residue, a residue derived from naturally occurring α-amino acid, particularly amino acid constituting proteins, for example, an aliphatic amino acid such as glycine or alanine; branched amino acid such as valine, leucine or isoleucine; hydroxylated amino acid such as serine or threonine; acidic amino acid such as aspartic acid or glutamic acid; amide such as asparagine or glutamine; alkaline amino acid such as lysine, hydroxylysine or arginine; sulfur containing amino acid such as cysteine, cystine or methionine; aromatic amino acid such as phenylalanine or tyrosine; heterocylic amino acid such as tryptophan or histidine, and imino acid such as proline or hydroxyproline are preferred. The hydrogen atom or the residue of amino acid derivative bonded to the α-amino group or imino group of the amino acid residue [represented by X—] is not particularly limited with respect to the kind and the chain length of peptide of the constituent amino acid residue, provided that it can be peptide bonded through single amino acid or α-amino group, and further, phosphoric acid, sugar or other substituent may be covalently bonded to the constituent amino acid residue, and it may form a conjugated with a lipid. In each corresponding constitute amino acid residue, the substituents may be as follows. More specifically, as the substituent on the guanidino group of arginine residue there may be included alkyl groups such as methyl, ethyl, etc., the substituents derived from adenosine diphosphate ribose, citrulline, ornithine, etc. As the substituent on the ε-amino group of lysine residue there may be included the substituents derived from compounds having glycosyl group, pyridoxyl group, biotinyl group, lipoyl group, acetyl group, phosphoric acid or δ-hydroxyl group, compounds having δ-glycosyl group, glutaraldehyde or anhydrous citraconic acid, etc. As the substituent on the imidazole group of hystidine residue, there may included methyl group, the substituents derived from phosphoric acid, iodine or flavin, etc. As the substituent on proline residue, there may be included hydroxyl group, dihydroxyl group, glycosyl group, etc. As the substituent on the benzene ring of phenylalanine residue, there may be included hydroxyl group, glycosyl group, etc. As the substituent on the hydroxyl group of tyrosine group, there may be included glycosyloxy group, sulfonic acid group, iodine atom, bromine atom, chlorine atom, the substituents derived from compounds having hydroxyl group, bisether, adenine, uridine or RNA (ribonucleic acid), etc. As the substituent on the hydroxyl group of serine residue, there may included methyl group, glycosyl group, the substituents derived from phosphopanteteic acid, adenosine diphosphoric acid ribose or phosphoric acid, etc. As the substituent on the hydroxyl group of threonine residue, there may be included glycosyl group, methyl group, the substituents derived from phosphoric acid, etc. As the substituent on the SH group of cysteine residue, there may be included glycosyl group, the substituents derived from cystine, dehydroalanine, heme, flavin or selenium, etc. As the substituent on the carboxyl group of aspartic acid or glutamic acid residue, there may be included methyl group, the substituents derived from phosphoric acid or compounds having γ-carboxyl group. As the subsituent on the amide group of asparagine or glutamine residue, there may be included the substituents derived from compounds having glycosyl group, pyrrolidonyl group or imino group, etc.

The peptide having glycine peptide bonded to the C-terminal residue or its derivative as the above substrate may be either one extracted from nature, one produced by chemical synthesis or one produced by use of the recombinant DNA technique.

Thus, the substrate represented by the formula (I) is a C-terminal glycine adduct, i.e., a peptide bonded compound between amino group of glycine and C-terminal carboxyl group of any peptides, for example, peptides with amino acid residues of about 2 to 100, phosphate peptides as represented by casein, protein kinase, adenovirus EIA protein, RAS1 protein, etc. and hydrolyzates thereof, lipoproteins such as thromboplastin, $\alpha_1$-lipoprotein, lipovitellin, etc. and hydrolyzates thereof, metal proteins as represented by hemoglobin, myoglobin, hemocyanin, chlorophyl, phycocyanine, flavin, rhodopsin, etc., and hydrolyzates thereof, glycoproteins as represented by collagen, laminine, interferon α, seroglycolide, avidin, etc. and hydrolyzates thereof, as well as other peptides formed a maturation peptide having physiological activity, for example calcitonin, secretin, gastrin, vasoactive intestinal peptide, cholecystokinin, caerulein, pancreatic polypeptide, growth hormone-releasing factor, corticotropin-releasing factor, calcitonin gene related peptide, etc., with amidation. Of these, a preferable substrate for identification enzyme activity of the enzyme composition may include D-tyrosyl-valyl-glycine (D-Tyr-Val-Gly), D-tyrosyl-tryptophanyl-glycine (D-Tyr-Trp-Gly), glycyl-phenylalanyl-glycine (Gly-Phe-Gly), phenylalanyl-glycyl-phenylalanyl-glycine (Phe-Gly-Phe-Gly), D-tyrosyl-leucyl-asparaginyl-glycine (D-Tyr-Leu-Asn-Gly), arginyl-phenylalanyl-glycine (Arg-Phe-Gly), arginyl-alanyl-arginyl-leucyl-glycine (Arg-Ala-Arg-Leu-Gly), leucyl-methionyl-glycine (Leu-Met-Gly), glycyl-leucyl-methionyl-glycine (Gly-Leu-Met-Gly), phenylalanyl-glycyl-leucyl-methionyl-glycine (Phe-Gly-Leu-Met-Gly), asparaginyl-arginyl-phenylalanyl-glycine (Asp-Arg-Phe-Gly), tryptophanyl-asparaginyl-arginyl-phenylalanyl-glycine (Trp-Asp-Arg-Phe-Gly), alanyl-phenylalanyl-glycine (Ala-Phe-Gly), lysyl-alanyl-phenylalanyl-glycine (Lys-Ala-Phe-Gly), seryl-lysylalanylphenylalanyl-glycine (Ser-Lys-Ala-Phe-Gly), arginyl-tyrosyl-glycine (Arg-Tyr-Gly), glycyl-methionyl-glycine (Gly-Met-Gly), glycyl-tyrosyl-glycine (Gly-Tyr-Gly), glycyl-histidyl-glycine (Gly-His-Gly), histidyl-glycylglycine (His-Gly-Gly), tryptophanyl-glycyl-glycine (Trp-Gly-Gly) and glycyl-cystenyl-glycine (Gly-Cys-Gly), etc. (except for glycine, L-form is shown unless otherwise particularly noted as D—). On the other hand, a preferable substrate for using the enzyme composition, the third present invention, may include the above peptides forming a maturation peptide having a physiological activity with amidation.

Acting on these substrates to participate in the reaction for forming the C-terminal amidated product represented by the following formula:

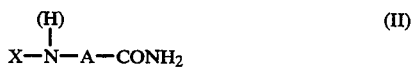

(wherein A and X have the above meanings) and glyoxylic acid means to promote the main reaction step for converting the substrate of the formula (I) to the C-terminal amidated product of the formula (II), which is the concept also including the case when catalyzing formation of precursor caused the C-terminal amidated a product represented by the formula (II), and converting the precursor into the compound of the formula (II) through conventional hydrolysis reaction, etc.

The purity which does not have a substantially bad influence on the above formation reaction means that when intervening proteinaceous components are co-present in the enzyme composition of the present invention, they do not have a bad influence on separation and purification in conventional manner of the product represented by the formula (II). Specifically, when analyzed by HPLC, the peak derived from the enzyme composition of the present invention becomes much smaller compared with the amidated product represented by the above formula (II), whereby the product represented by the formula (II) can be isolated more easily by conventional peptide or protein separation and purification means. More specifically, this means to have an enzyme purity such that, when the reaction is carried out at 37° C. for 5 hours, and an enzyme composition is added in an amount which converts 50% or more of the substrate of the above reaction system (I) to the product of the formula (II), the peak of the protein formed from said enzyme composition becomes 20% or less of the above product peak. In other words, with the specific activity of the above reaction derived from porcine or horse serum as the standard, its specific activity is elevated to about 150-fold. Specific activity refers to activity per 1 mg of protein under the reaction conditions as described below.

The animals from which serum and plasma are derived as the source of supply of the C-terminal amidating enzyme composition in the present invention may include mammals such as human, bovine, horse, porcine, sheep, rabbit, goat, rat, mouse, etc.; arian such as chicken, turkey, etc.; batrachian such as frog, etc.; reptiles such as snake; fish such as sardine, mackerel, eel, salmon, etc. Serum and plasma may be either prepared directly from blood or commercially available. For preparation from blood, the following method may be employed. Concerning blood collection, the methods generally used as described in, for example, "Seikagaku Handbook, p. 723-725" (written by Suzuki, Maruzen (1984) may be employed. However, when obtaining serum, anticoagulants such as heparin, ethylenediaminetetraacetic acid and their sodium salts, and sodium citrate, must not be used. The preparation of serum may be conducted as described in, for example, "Zoku Seikagaku Jikken Kouza, Vol. 5, p. 9" written by Matsumoto et al, Tokyo Kagakudojin (1986) or "Zoku Seikagaku Jikken Kouza, Vol. 8, Latter vol., p. 682", written by Matsumoto et al, Tokyo Kagaku Dojin (1987). For example, it can be accomplished by leaving the blood to stand at 20° to 40° C. for at least 30 minutes to sufficiently sediment blood clots, and recovering the supernatant. When recovering the supernatant, if necessary, centrifugation, filtration, etc. may be performed. As for preparation of plasma, it can be accomplished as described in, for example, "Seibutsugaku Jiten, Second ed., p. 332-333", Iwanami (1977), by adding the above anticoagulant during blooding or immediately after blooding, or after inhibiting progress of blood coagulation by leaving it to stand at a low temperature of 0° to 10° C. for at least 10 minutes, sedimenting concrete components and recovering the supernatant. Also in this case, if necessary, centrifugation, filtration, etc. may be conducted. Serum and plasma are stored at low temperatures of $-80°$ C. to 10° C., but the activity of the C-terninal amidating enzyme composition will not be lowered by freezing and thawing for several times.

The amidating enzyme composition is further specified by the following physicochemical properties. That is:

(i) the optimum pH is about 6.0 and stable pH is 5 to 9;

(ii) the acting optimum temperature is within the range from about 25° to 40° C.;

(iii) metal ions and L-ascorbic acid are acted as the cofactor;

(iv) said composition has a molecular weight of about 50,000 and/or about 100,000 as determined according to the molecular weight determination by gel filtration;

(v) said composition has an isoelectric point of pH about 4.5 and/or about 6.7 according to isoelectric point chromatography; and (vi) said action is activated by addition of catalase.

The above properties (i) and (ii) are measured by use of buffers conventionally used, specifically tris-HCl, mes-potassium hydroxide, tes-sodium hydroxide, hepes-potassium hydroxide buffer. The enzyme composition of the present invention can catalyze the above reaction within the temperature range of 1° C. to 55° C., but will be inactivated at 56° C. within about 10 minutes, and also slight inactivation is seen at around 45° C.

As the metal ion, $Cu^{2+}$, $Ni^{2+}$, $CO^{2+}$, $Fe^{3+}$, etc. may be suitable, particularly preferably $Cu^{2+}$. These metal ions and L-ascorbic acid may be considered to function as cofactor. Also, the reducing agents such as NADH or NADPH and the catecholamines such as dopamine or norepinephrine may act as L-ascorbic acid.

Additionally, the present enzyme composition which may have the above described physicochemical properties and mixture including the plural enzymatic active substances, whereas it's active substance (or enzyme per se) may be separated independently from other, i.e., consisting of any one of active substances having a molecular weight of of about 50,000 and about 100,000.

The molecular weight is the value measured according of the gel filtration method know per se [e.g. "Seikagaku Jikken Kouza 5, Enzyme Study Method, Former vol., p. 283–298, Tokyo Kagaku Dojin (1975)]. Specifically, by use of a 50 mM tris-HCl (pH 7.4) containing 100 mM potassium chloride as the equilibration and elution solution, gel filtration was effected on Toyopearl HW-55S (produced by Toso), and the molecular weight was determined with β-amylase (M.W. 200,000), alcohol dehydrogenase (M.W. 150,000), BSA (M.W. 66,000), carbonic anhydrolase (M.W. 29,000) and cytochrome C (M.W.15,400) as the indices.

The isoelectric point is the value measured according to the isoelectric point chromatography known per se (chromatofocusting) [e.g. "Zoku Seikagaku Jikken Kouza 2, Chemistry of Proteins, Former vol., p. 160–171", Tokyo Kagaku Dojin (1987)]. Specifically, by use of MonoP column (0.5×20 cm) (produced by Pharmacia), the column was equilibrated with 25 mM imidazole-HCl buffer (pH 7.4), added with a sample substituted with the same buffer solvent system and then elution was effected with Polybuffer 74 (produced by Pharmacia: diluted to 8-fold, adjusted to pH 4.0 with hydrochloric acid) for measurement.

Process for Producing the Enzyme Composition

The enzyme composition of the present invention as described above can be obtained according to the process described below. That is, it can be obtained by treating a serum or a plasma with the substrate affinity chromatography using the C-terminal glycine adduct represented by the above formula (I) as the ligand, used optionally in combination the method conventionally used, such as:

(1) fractionation by precipitation;
(2) heparin affinity chromatography; and/or
(3) removal of low molecular weight substances by dialysis, gel filtration, etc.

As the ligand of the present invention, all of the C-terminal glycine adducts represented by the above formula (I) can be used, but preferably they include the peptides comprising 2 to 6 amino acid residues including glycines as specifically a preferable substrate for identification enzyme activity of the present enzyme composition mentioned above. Among them, D-Tyr-Trp-Gly, Phe-Gly-Phe-Gly and Gly-Phe-Gly are more preferable, but that using Phe-Gly-Phe-Gly as the ligand is particularly preferred as having a strong affinity for the enzyme composition of the present invention.

These ligands are generally used as bound to a water-insoluble carrier, and it is important that the carboxyl group of the C-terminal glycine reside of the peptide to be used as the ligand should be under free state for bonding to the C-terminal amidating enzyme, and it is required to be bound to the carrier through the amino group of the amino acid reside at N-end. In other words, the carrier may be any one which can be bound to the amino group of the peptide, and an active group reactive with the amino group may be chemically introduced into the carrier, or alternatively a commercially available carrier having already introduced the active group may be used. The method for introducing chemically may be the method generally employed. For example, as described in "Seikagaku Jikkenhou, Vol 5, Former vol., p. 257–281" written by Kasai, Tokyo Kagaku Dojin (1975), imidocarboxyl group is introduced into agarose by use of cyan bromide. Commercially available activated carriers may include agarose type, cellulose type, hydrophilic polyvinyl type, etc. with the substrate as the index, but any of these may be employed. As the agarose type carrier, there may be included CNBr activated Sepharose 4B (produced by Pharmacia) in which the CNBr method is used for binding the ligand with the amino group, CH-Sepharose 4B, ECH-Sepharose 4B (all produced by Pharmacia) by use of the carbodiimide method, Affigel 10, Affigel 15 (all are produced by Biorad), the tresyl activated Sepharose 4B (produced by Parmacia) by use of the tresyl chloride method, etc. As the cellulose type carrier, Formylcellulofine (produced by Chisso) by using the formyl method may be included. As the hydrophilic polyvinyl type carrier, there may be included AF-carboxytoyopearl 650 by use of the carbodiimide method, AF-formyltoyopearl 650 by using the. formyl method, AF-tresyltoyopearl 650 by using the tresyl chloride method, AF-epoxytoyopearl 650 by using the epoxy activation method (all are produced by Toso)., etc. The binding reaction with the ligand may be carried out according to the instructions for each carrier.

Of these, the method of preparing Affigel 10 is described. The reaction between Affigel 10 and the peptide is carried out in a buffer such as Mops-potassium hydroxide, etc. of 0,001 to 1M, preferably 0.1M. The reaction conditions can be 0° to 20° C., 10 minutes to 24 hours and about pH 3 to 11, but preferably are 4° C., 4 to 24 hours and pH 5 to 9. The mixing ratio of Affigel 10 to the peptide to be used for binding may be within the range of about 25 μmol per 1 ml of Affigel, because more will be bound as the peptide is added in a larger amount within this range, but conveniently about 1 to 20 μmol may be used with respect to the binding efficiency. After the reaction, the mixture is thoroughly washed with the buffer used during the reaction, and then tris-HCl (pH 8.0) is added to the final concentration of 50 mM and the unreacted active groups are blocked according to the method of shaking, at 4° C. for one hour, etc. Thus, the substrate affinity gel is prepared.

The substrate affinity chromatography may be carried out either batchwise or continuously with the gel packed in a column. The time for contacting the sample with the gel may be such that the C-terminal amidating enzyme can be sufficiently adsorbed, but may be generally 20 minutes to 24 hours. Nonadsorbed components are washed away with a buffer having the same composition as that used for equilibration of the gel with a low ionic strength and pH of 6.0 to 11.0, preferably 7.0 to 9.0, for example, 10 mM hepes-potassium hydroxide (pH 7.0). Thereafter, the fractions in which the C-terminal amidating enzyme activity exists are eluted. The eluting solution may have any composition which can give the C-terminal amidating enzyme with a good efficiency, but preferable examples include buffers with pH between 7.0 and 9.0 containing about 1 to 40% of acetonitrile together with 0.1 to 1M sodium chloride, such as 10 mM hepes-sodium hydroxide (pH 7.0) containing 20% of acetonitrile and 0.4M sodium chloride. Also, when filled in the column, elusion may be carried out with application of the concentration gradient.

In some cases, before or after practicing the above substrate affinity chromatography [hereinafter represented by (4)], or both before and after, the fractionation by way of precipitation as mentioned above [hereinafter represented by (1)], heparin affinity chromatography [hereinafter represented by (2)] and/or the step of removing low molecular weight substances by dialysis, gel filtration, etc. [hereinafter represented by (3)] may be also practiced. Generally speaking, it is preferable to practice the total number of 1 to 6 steps, and further the above step (4) or (3) as the final step. Specific examples of the combination of the respective steps may include only (4), (1)→(4), (4)→(3), (2)→(4), (1)→(3)→(4), (2)→(3)→(4), (1)→(4)→(3), (2)→(4)→(3), (2)→(1)→(4), (1)→(2)→(3)→(4), (1)→(2)→(4)→(3), (1)→(3)→(4)→(3), (1)→(2)→(1)→(4), (1)→(2)→(1)→(3)→(4), (2)→(1)→(4)→(3), (2)→(1)→(3)→(4), (2)→(1)→(3)→(4)→(3), (1)→(2)→(3)→(4)→(3), (1)→(3)→(2)→(3)→(4), (1)→(3)→(2)→(3)→(4)→(3), (4)→(3)→(4), (4)→(3)→(4)→(3) or (1)→(4)→(3)→(4)→(3), etc. Among them, it is preferred that the steps should proceed in the order of (1)→(2)→(3)→(4), (1)→(2)→(3)→(4)→(3), (1)→(3)→(2)→(3)→(4) or (1)→(3)→(2)→(3)→(4)→(3).

In the following, the above steps (1) to (3) are described. These steps are all carried out at 0° C. to 10° C., preferably 4° C.

As the substance to be used for fractionation according to precipitation of (1), there may be included salts such as ammonium sulfate, etc., organic solvents such as ethanol, acetone, etc., polymers such as polyethylene glycol etc. The concentration added is not particularly limited, but it is preferable to use the conditions under which the C-terminal amidating enzyme can be recovered with a good efficiency, and can be separated from other protein components. For example, when 30 to 50% of saturated ammonium sulfate, 10 to 15% (w/v) of polyethylene glycol 6000 are added, the C-terminal amidating enzyme comes into the precipitated fraction, while albumin contained in much amount in serum and plasma exists in the supernatant portion, whereby purification can be effected with a good efficiency. Addition may be preferably done gradually while stirring with a stirrer. After the mixture is left to stand for at least one hour after completion of the addition, the fractions in which the C-terminal amidating enzyme exists are recovered. When the precipitated fraction is recovered, this is dissolved in an appropriate buffer. The buffer, provided that it has pH 6.0 to 11.0, preferably pH 7.0 to 9.0, may have any composition, including, for example, tris-HCl hepes-potassium hydroxide, tes-sodium hydroxide, etc. The concentration is not particularly limited within the range which can maintain the buffering ability, but is preferably about 5 to 50 mM.

The active fraction obtained according to (1) may be subjected again to (1) or proceed to any step of (2) to (4), but when proceeding to (2) or (4) by using a salt such as ammonium sulfate for fractionation of (1), it is necessary to lower the salt concentration to a level at which the C-terminal amidating enzyme can be bound to the gel used in the step of (3) or in the subsequent step with addition of an appropriate buffer. On the other hand, when the precipitates are dissolved and left to stand for one hour or longer, or when dialysis is performed, insoluble substances may be formed, which are removed by centrifugation or filtration.

As for heparin affinity chromatography of (2), it may be carried out either batchwise or continuously by filling the gel in a column. Commercially available gels having heparin as the ligand may include heparin Sepharose CL-6B (produced by Pharmacia), Affigel heparin (produced by Biorad), heparin Agarose (produced by Sigma), AF-heparintoyopearl 650 (produced by Toso).

Serum or plasma is contacted directly, or after the treatment of the fraction by precipitation as shown in (1), with the heparin affinity gel. The contact time may be such that the C-terminal amidating enzyme can be sufficiently adsorbed, but generally 20 minutes to 12 hours. The components having no affinity for heparin are removed with a buffer having a low ionic strength to the extent that no C-terminal amidating enzyme is eluted with pH of 6.0 to 11.0, preferably 7.0.to 9.0, for example, 10 mM hepes-potassium hydroxide (pH 7.0). Thereafter, the fractions containing the C-terminal amidating enzyme are eluted. As the eluting solution, one having a higher recovery of the C-terminal amidating enzyme activity is preferred. For example, one having pH 6.0 to 11.0 containing a salt generally used for enzyme purification such as 0.5M–2M sodium chloride, potassium chloride, ammonium sulfate, etc. Elution may be performed according to the salt concentration gradient when packed in a column, but one step elution is preferred for a higher recovery. For example, elution may be effected with 10 mM hepes-potassium hydroxide buffer (pH 7.0) containing 0.3–2.0M sodium chloride.

The active fraction obtained in the step (2) may be also provided subsequently for any of the steps (1) to (4) but when the step (2) is performed again, or when proceeding to the step (4), the step (3) may be previously conducted, or the ionic strength lowered to a level at which the C-terminal amidating enzyme can be adsorbed to the gel used in (2), (4) by addition of a large amount of a buffer of 50 mM or lower having a low ionic strength and pH 6.0 to 11.0, preferably 7.0 to 9.0, for example, 5 mM hepes-potassium hydroxide (pH 7.0), etc.

As for the step of removing low molecular weight substances by dialysis, gel filtration, etc. of (3), in the case of dialysis, the membrane to be used may have a cut-off molecular weight to the extent that the C-terminal amidating enzyme cannot pass therethrough, but is preferably 1,000 to 10,000. The method of dialysis may be one generally employed as described in, for example, "Seikagaku Jikken Kouza, Vol. 5, Former vol., p. 252–253", written by Soda, Tokyo Kagaku Dojin (1975), and may be carried out for several hours to several days, against a buffer with low ionic strength having pH 6.0 to 11.0, preferably pH 7.0 to 9.0, such as 10 mM hepes-potassium hydroxide (pH 7.0), 10 mM tris-HCl (pH 7.5), etc. Also, during dialysis, when insoluble substances are precipitated, they are removed by, for example, centrifugation, filtration, etc.

Concerning gel filtration, any carrier generally used for gel filtration may be employed. It is preferable that, for example, Sephadex G-10, G-15, G-25, G-50, G-75, G-100, Sephacryl S-200, S-300 (all produced by Pharmacia), Toyopearl HW-40 (produced by Toso), Biogel P-2, P-4, P-6 (all produced by Biorad), etc. The buffer to be used may have the same composition as that used during dialysis. However, if the ionic strength is too low, it may be considered that adsorption of the C-terminal amidating enzyme onto the gel may occur, and therefore the concentration is made 5 to 200 preferably 10 to 20 nM. The method of gel filtration may be practiced as described in, for example, "Seikagaku Jikken Kouza, Vol. 5, Former vol., p. 283–298", written by Soda, Tokyo Kagaku Dojin (1975). After a sample is added in an amount sufficient to obtain separation capacity relative to the bed volume of the gel filtration carrier (20% or less of the bed volume), elution is effected and the fraction in which the C-terminal amidating enzyme activity exists is recovered.

The active fraction obtained by the step of (3) can be permitted to proceed to the respective steps of (1) to (4) without any particular treatment. Also, such an enzyme composition is isolated according to the method of gel filtration to purify a protein, and may be an enzyme composition having individually a single molecular weight of about 50,000 and 100,000.

The respective steps as described above can be practiced by following the C-terminal amidating enzyme activity to obtain active fractions.

An assay of the C-terminal amidating enzyme activity may be carried out by any method which can confirm the amidated reaction, for example the method of Eipper et al in which $^{125}$I-D-tyrosyl-valyl-glycine ($^{125}$I-D-Tyr-Val-Gly) is allowed to react as the substrate, and the substrate is separated from the reaction product by ion exchange chromatography (Eipper et al, Pro. Natl, Acad. Sci., U.S.A., 80, 5144, 1983) or the method of Mizuno et al in which $^{125}$I-Ac-tyrosyl-phenylalanyl-glycine ($^{125}$I-Ac-Tyr-Phe-Gly) is allowed to react as the substrate, and the reaction product is extracted with ethyl acetate (Mizuno et al, Biochem. Biophys. Res. Commun., 137, 984, 1986), or the method of Jones et al in which N-dansyl-tyrosyl-valyl-glycine (N-dansyl-Tyr-Val-Gly) is allowed to react as the substrate, and the substrate is separated from the reaction product by high performance liquid chromatography (HPLC) (Jones et al, Anal. Blochem., 168, 272, 1988), or the method of Ramer et al in which the glyoxylic acid which is the enzyme reaction product is quantitated (Ramer et al, J. Am., Chem. Soc., 110, 8526, 1988), etc. The method of assaying the C-terminal amidating enzyme activity according to the above method of Eipper et al used in the present invention is described in detail.

Method of assaying enzyme activity

The reaction solution was prepared by adding 50 mM hepes-potassium hydroxide buffer (pH 7.0), 10 μM copper sulfate, 1.5 mM L-ascorbic acid, 4 μg catalase (produced by Sigma), 2 μM D-Tyr-Val-Gly, 20,000 cpm $^{125}$I-D-Tyr-Val-Gly and the C-terminal amidating enzyme solution, and making the total amount to 80 μl with water. The reaction mixture was subjected to the reaction at 37° C. in a thermostat water tank under stirring for 2 hours or 5 hours. The reaction was stopped by addition of one ml of 2 mM sodium phosphate buffer (pH 5.0). The substrate was separated from the reaction product through SP-Sephadex C-50 (produced by Pharmacia) ion exchange chromatography. The reaction mixture was passed through ion exchange gel with a bed volume of 2 ml, and the unreacted substrate was washed away with 10 ml of 2 mM sodium phosphate buffer (Solution A) to have only the reaction product adsorbed onto the gel. Next, using 2.5 ml of a 50 mM sodium phosphate buffer (pH 5.0) containing 0.5M sodium chloride, the reaction product was eluted (Solution B). The radioactivities of Solution A and Solution B were measured by a γ-counter and the substrate conversion was determined from the following formula.

$$\text{Substrate conversion (\%)} = \frac{\text{Radioactivity of Solution B}}{\text{Radioactivity of Solution A} + \text{Radioactivity of Solution B}} \times 100$$

The enzyme activity 1 (U) is defined as the activity which converts 1 pmol of the substrate per one hour.

The specific activity is defined as the activity per 1 mg of protein.

Use of the Enzyme Composition

In addition, the present invention discloses the third invention related to the use of the enzyme composition of the present invention described above, i.e., a method of producing a C-terminal amidated compound by the formula (II), which comprises treating a C-terminal glycine adduct represented by the formula (I) with the above enzyme composition, a serum or plasma of horse or porcine.

In the method according to the present invention, preferably an enzyme composition of the present invention is used, since it is almost eliminated in an admixed protein, also a serum or plasma of horse or porcine, and a concentrate derived therefrom may be used, although the latter may require an intricate purifying process to obtain an end product.

The C-terminal glycine adducts represented by the formula (I) may be a compound described above, particularly a compound which substituted a C-terminal carbamoyl group ($-CONH_2$) of a compound represented by the formula (II) for a peptide bonded group ($-CONHCH_2COOH$) between the C-terminal carboxyl group and the amino group in glycine, and the compound represented by the formula (II) may be included arginine vasotocin (AVT), lutenizing hormone-release hormone (LH-RH), oxytocin, gastrin, gastrin secretion promoting peptide (GGRP), calcitonin (CT), vasoactive intestinal peptide (VIP), thyrotropin-releasing hormone (TRH), melanophore stimulating hormone (MSH), MSH release inhibiting hormone (MIH), cholecystokininoctapeptide (CCK-8), substance P (SP), adipokinin, pancreatic polypeptide (PP), growth hormone releasing factor, secretin, caerulein, mollusk cardiostimulant neuropeptide, vasopressin, adrenocorticotropic hormone (ACTH), allochroic hormone, bombesin, light adaptation hormone, motilin, apamin, allitecine, eredoicin, catcinin, granulibelline R, scotophobin, hyranbatecaerulein, obesity cell degranulation peptide, physaremin, phyllocaerulein, phyllomezcin, promellitin, bombinin, mastoballan, manitoballan-X, mellitin-1, lanatensin; lanatensin-R, etc. The above compounds can be produced by peptide synthesis or a recombinant DNA technique known per se.

The treating may be carried out in a common buffer, preferably in the presence of a metal ion, L-ascorbic acid and others, and catalased in appropriate amounts, respectively.

The compound represented by the formula (I) (or substrate) concentration in the buffer is not particularly limited, but can be varied as desired, generally suitably about 0.1 μM to 2 mM.

The pH of the buffer is preferably 5 to 10, more preferably around pH 7. The buffering agent for preparing such buffer is not particularly limited, but those conventionally used may be employed. For example, Tris-HCl, Hepes-potassium hydroxide may be included. The concentration of the buffering agent in the buffer may be any concentration, provided that the buffering action can be achieved, but is preferably 20 to 200 mM.

As the metal ion, $Cu^{2+}$, $Ni^{2+}$, $Co^{2+}$, $Fe^{3+}$, etc. is preferable, particularly preferably $Cu^{2+}$. The concentration of the metal ion in the buffer may be suitably 0 to 1000 μM, preferably 0 to 200 μM, more preferably 0.01 to 50 μM. The compounds for providing such metal ion are not particularly limited but may include CuSO₄, CuCl₂, NiCl₂, CoCl₂, FeCl₃, etc.

L-ascorbic acid and others may be included the reducing agents such as L-ascorbic acid, NADH or NADPH, and the catecholamines such as dopamine or norepinephrine.

The concentration of L-ascorbic acid in the buffer may be suitably 0 to 10 mM, particularly 0.5 to 2 mM.

The concentration of catalase in the buffer may be suitably 0 to 300 μg/ml, preferably 10 to 200 μg/ml, more preferably 40 to 100 μg/ml.

The amount of the present enzyme composition and serum or plasma obtained from horse or porcine employed is not particularly limited and can be varied, but suitably contains an amidation enzyme activity of a pmol/hr or more, more preferably 10×a pmol/hr or more, most preferably 10×a pmol/hr to a mol/hr [units indicate enzyme activity, amount of the substrate which can be reacted at 37° C. for one hour (e.g., represented in terms of pmol)], based on the amount of the substrate existing in the reaction system (defined as a nmol).

The enzyme reaction may be carried out stationarily or under shaking at 1° to 55° C., preferably 25° to 40° C., most preferably around 37° C. The reaction is completed generally within one minute to 48 hours.

Separation, purification of the compound represented by the formula (II) derived from the said treating can be carried out by ion exchange chromatography, reverse phase chromatography, gel filtration, affinity chromatography, high performance liquid chromatography (HPLC), thin layer chromatography (TLC), etc. The substrate and the amidated product have C-termini which are carboxyl group and amide group, respectively, thus differing in charges. Ion exchange chromatography, reverse phase chromatography by utilizing this property may be suitable. Also, affinity chromatography using the antibody of the product is effective.

The present invention is described in more detail below with reference to Examples. The present invention is not limited at all by these Examples.

EXAMPLE 1

Preparation of Gel for Substrate Affinity Chromatography

An amount 5 ml of Affigel 10 was measured into a 10 ml volume Econocolumn (produced by Biorad) filled with isopropanol. After isopropanol was washed out, the gel was washed with 50 ml of 10 mM sodium acetate buffer (pH 4.5) and then with 10 ml of 0.1M Mops-sodium hydroxide buffer (containing 80 mM calcium chloride, pH 7.5). After the gel was transferred into a bottle of 20 ml volume, it was mixed with 10 ml of the above Mops-sodium hydroxide buffer containing 40 mg (about 100 μmol) of phenylalanyl-glycyl-phenylalanyl-glycine (Phe-Gly-Phe-Gly, produced by Sigma) dissolved therein and the shaking reaction was carried out at 4° C. for 18 hours. Then, 0.5 ml of 1M tris-HCl buffer (pH 8.0) was added and the shaking reaction was carried out at 4° C. for one hour to deactivate the unreacted active groups. After the gel was washed with deionized water, it was suspended in 0.02% NaN₃, filled in a column and stored at 4° C. From the amount of the peptide (Phe-Gly-Phe-Gly) provided for the reaction and the peptide amount in the solution, about 10 μmol per 1 ml of gel was calculated to be bound.

EXAMPLE 2

Preparation of C-terminal Amidating Enzyme Composition from Horse Serum (1) To 100 ml of a commercially available horse serum (produced by Gibco) was gradually added under stirring 100 ml of a 25% aqueous polyethylene glycol 6000 (produced by Wako Junyaku), namely to a concentration of 12.5%. The following operations were all conducted at 4° C. After standing for 12 hours, the mixture was centrifuged (10,000×g, 10 min.) and the resultant precipitates were dissolved in 120 ml of hepes-potassium hydroxide buffer (pH 7.0). Further after standing for 2 hours, the insoluble substance formed was again removed by centrifugation (10,000×g, 10 min.) to obtain a supernatant containing the C-terminal amidating enzyme activity (127 ml).

(2) The active fraction obtained in the above (1) was applied to a column (1.6×15 cm) filled with heparin Sepharose CL-6B (produced by Pharmacia) equilibrated with 10 mM hepes-potassium hydroxide buffer (pH 7.0). After the nonadsorbed substances were washed out with 96 ml of the same buffer elution was effected with 10 mM hepes-potassium hydroxide buffer (pH 7.0) containing 0.5M sodium chloride (flow rate 30 ml/hr). FIG. 1 shows the elution pattern. The C-terminal amidating enzyme was eluted with 0.5M sodium chloride containing buffer (fraction Nos. 14–16), but since No. 14 contained a large amount of proteins and had a low specific activity, No. 15, 16 were collected (16 ml).

(3) The above fractions were dialyzed once against one liter of 10 mM hepes-potassium hydroxide buffer (pH 7.0) by use of Spectra/pore dialysis membrane (cut-off molecular weight 3500, Spectrum) for 12 hours.

(4) Affigel 10-Phe-Gly-Phe-Gly gel (5 ml) was filled in a column (1.0×6.3 cm), and the column was equilibrated with 10 mM hepes-potassium hydroxide buffer (pH 7.0) containing 0.1M sodium chloride. To the column was applied the sample (18.1 ml) obtained in the above (3). To ensure that the C-terminal amidating enzyme was adsorbed onto the gel, the liquid passed through the column was circulated many times through the column (flow rate 20 ml/hr). After 12 hours, the circulation was stopped, and the nonadsorbed substances were washed out with 35 ml of the buffer used for equilibration, followed by elution with 8 mM hepes-potassium hydroxide buffer (pH 7.0) containing 0.4M sodium chloride and 20% acetonitrile (flow rate 20 ml/hr). The C-terminal amidating enzyme activity was recognized only in the eluted fraction (2.5 ml).

Table 1 shows the total protein amounts, the total enzyme activities, specific activities, yields and purification folds in the respective steps of purification conducted in the above (1) to (4).

TABLE 1

| | Preparation of C-terminal amidating enzyme composition from horse serum | | | | |
|---|---|---|---|---|---|
| Steps | Total protein (mg) | Total activity (U) | Specific activity (U/mg) | Yield (%) | Purification fold |
| Serum | 7100 | 199500 | 28 | (100) | (1.0) |

TABLE 1-continued

Preparation of C-terminal amidating enzyme composition from horse serum

| Steps | Total protein (mg) | Total activity (U) | Specific activity (U/mg) | Yield (%) | Purification fold |
|---|---|---|---|---|---|
| (1) Polyethylene glycol 6000 precipitation | 5101 | 195072 | 38 | 98 | 1.4 |
| (2) heparin-Sepharose CL-6B | 328.2 | 62566 | 191 | 32 | 6.8 |
| (3) Dialysis | 281.9 | 67018 | 238 | 34 | 8.5 |
| (4) Affigel 10-Phe—Gly—Phe—Gly | 3.03 | 15120 | 4990 | 7.6 | 178 |

A measurement of the protein amount was conducted by using the improved method of Lowry (Bensadoun et al, Anal. Blochem., 70, 265, 1976), and the standard curve was prepared with bovine serum albumin (fraction V, produced by Sigma).

As shown in Table 1, the C-terminal amidating enzyme was purified to 178-fold with a yield of 7.6%.

The purified enzymatic activity is increased by an introduction of acetonitrile into the reaction mixture. For example, the activity is increased twofold as the specific activity having about 9000 U/mg, when acetonitrile is put into the enzymatic sample of the step (4) in table 1 to 10% by volume based on the whole of the reaction mixture. Also, the specific activity is increased approximately seven fold according to the same enzymatic sample, 4000 U/mg to 28000 U/mg, when an enzymatic reaction was carried out in 7.5% acetonitrile instead of 0% acetonitrile with 100 μM Phe-Gly-Phe-Gly (a total of 200 μl reaction mixture), and the specific activity was determined by the HPLC method.

EXAMPLE 3

Convert a Compound of the Formula (I) Into Formula (II) by Using the Enzyme Composition By using the C-terminal amidating enzyme preparation prepared according to Example 2 from a commercially available horse serum, the reaction was carried out with phenylalaninyl-glycyl-phenylalanyl-glycine (Phe-Gly-Phe-Gly) as the substrate. The composition of the reaction mixture was similar to that as described in the assaying method of enzyme activity. However, the substrate concentration was made 20 μM, the total volume 200 μl, the enzyme preparation used was 10 μl and 50 μl. The reaction product was detected by HPLC. The column used was Capcell Pak C8SG, 300 Å (produced by Shiseido). The eluting solvent used was 1 mM ammonium carbonate (pH 9.0) and acetonitrile, and a linear concentration gradient was applied to increase acetonitrile from 0% to 40%. The peptide was detected by the absorption at 214 nm. The results are shown in FIG. 2. (1) shows the result when the reaction was carried out for 5 hours with the use of an enzyme sample of 10 μl, and (2) that of 50 μl, and the peak at 11.2 min. is the unreacted Phe-Gly-Phe-Gly, and the peak at 15.2 min. the reaction product of phenylalanyl-glycyl-phenylalanine amide (Phe-GlY-Phe-NH$_2$). Conversion to the product was about 30% for (1) and about 100% for (2) as calculated from the ratio of the respective peak areas. In (2), the peak other than the product was 3% or less of the whole area ratio, if the peak derived from the solvent detected at around 1 min. is excluded.

EXAMPLES 4, 5 COMPARATIVE EXAMPLES 1-5

Convert a Compound of the Formula (I) Into Formula (II) by Use of Various Sera

C-terminal amidation enzymatic activities in sera of horse, porcine, bovine, rabbit, human, chicken and rat were assayed by use of D-tyrosyl-L-valyl-glycine (D-Tyr-Val-Gly) (produced by Sigma) as the compound of the formula (I) (substrate). Commercially available sera were used for 4 kinds of horse (produced by GIBCO), porcine (produced by Flow Lab), bovine (produced by M. A. Bioproducts) and chicken (produced by Flow Lab), and sera of rabbit, human and rat were prepared from blood. More specifically, each one ml of blood was taken, left to stand at 4° C. overnight and then centrifuged at 3000×g for 15 minutes. The supernatant thus obtained was provided for serum sample. For ease in detection of the compound of the formula (II) (amidated reaction product), tyrosine residues in the (substrate were labelled with $^{125}$I. In a 0.2M phosphate buffer (pH 7.2), 2.0 μg of D-Tyr-Val-Gly was mixed which 2 mCi radioactive iodine ($^{125}$I), and one Iodo bead (produced by Pirce Chemical) was added thereto to carry out the reaction for 5 minutes, followed by addition of 10 μl of mercaptoethanol to stop the reaction.

[$^{125}$I]-D-Tyr-Val-Gly was recovered by using HPLC (LC-6-A, produced by Shimazu Seisakusho). As the column, Capcell Pak C18SG, 120 Å 10 φ produced by Shiseido K. K. was used. Elution was conducted according to the concentration gradient of water and acetonitrile. A linear concentration gradient was applied for elution from 100% of an aqueous 0.1% trifluoroacetic acid (TFA), by mixing acetonitrile containing 0.09% gradually therewith periodically until acetonitrile became 40% after 90 minutes. At an acetonitrile concentration of about 20%, [$^{125}$I]-D-Tyr-Val-Gly could be detected as the peak of radioactivity. The peak was recovered by separation and lyophilized before use for the amidation reaction.

According to the method assaying enzyme activity described above, the amidation reaction mixture was prepared as follows. 50 mM Hepes-potassium hydroxide buffer (pH 7.0), 10 μM copper sulfate, 1.5 mM L-ascorbic acid, 4 μg catalase (produced by Sigma), 2 μM D-Tyr-Val-Gly, 20000 cpm [$^{125}$I]-D-Tyr-Val-Gly and 10 μl of various sera were mixed, and the total amount was made up to 80 μl. While the reaction mixture was shaken in a thermostat water tank of 37° C., the reaction was carried out for 2 hours or 5 hours. The reaction was stopped by addition of 1 ml of 2 mM sodium phosphate buffer (pH 5.0). The reaction product and the substrate were separated from each other by SP-Sephadex C-50

(produced by Pharmacia) ion exchange column chromatography. The reaction mixture was passed through an ion exchange gel with a bed volume of 2 ml, and the unreacted substrate was washed away with 10 ml of 2 mM sodium phosphate buffer (Solution A), thereby having only the reaction product adsorbed onto the gel. Next, using 2.5 ml of a 50 mM sodium phosphate buffer (pH 5.0) containing 0.5M sodium chloride, the reaction product was eluted (Solution B). Solutions A and B were respectively lyophilized, and the radioactivity peak was detected. As a result, it was confirmed that separation of the substrate from the reaction product was effected and that the amidation reaction had been correct, because the peak of [$^{125}$I]-D-Tyr-Val-NH$_2$ obtained by $^{125}$I labelling of Sigma reagent D-tyrosyl-L-valineamide (D-Tyr-Val-NH$_2$) coincided with the peak of Solution B and the peak of [$^{125}$I]-D-Tyr-Val-Gly with the peak of Solution A. The radioactivities of Solution A and Solution B were measured by $\gamma$-counter, and the substrate conversion ratio was determined from the formula as described above.

The protein mass in serum was measured according to the improved method of Lowry [Bensadoun et al, Anal, Blochem., 70, 265 (1976)]. At this time, the standard curve was prepared by using bovine serum albumin (produced by Sigma).

By using the protein measured, the substrate amount which can be converted in one hour per 1 mg of protein is shown as specific activity. The measurement results of various sera are summarized in Table 2.

TABLE 2

Amidation enzymatic activities of various sera

| | Organism species | Protein concentration (mg/ml serum) | Substrate conversion (%) Reaction time | | Specific activity (pmol/hr/mg) |
|---|---|---|---|---|---|
| | | | 2 hr | 5 hr | |
| Example 4 | Horse | 71 | 30.1 | 64.0 | 28 |
| Example 5 | Porcine | 79 | 21.2 | 53.2 | 21 |
| Comparative Example 1 | Human | 87 | 1.8 | 5.0 | 5 |
| Comparative Example 2 | Bovine | 42 | 2.2 | 5.6 | 5 |
| Comparative Example 3 | Rat | 51 | 1.5 | 4.1 | 4 |
| Comparative Example 4 | Rabbit | 64 | 2.6 | 6.3 | 6 |
| Comparative Example 5 | Chicken | 40 | 0.7 | 1.9 | 2 |

The amidation enzymatic activity was found in all the sera, but in Comparative Examples 1–5, the substrate conversion was as low as 5% even after the reaction for 5 hours, while in the horse and porcine of Examples 1 and 2, the conversion was found to exceed 50%. Also, with respect to a specific activity, Examples were found to be higher by 4 to 10-fold compared with Comparative Examples. Thus, horse and porcine sera per se, also, exhibited C-terminal amidating enzymatic activities which were sufficiently commercially available.

EXAMPLES 6,7, COMPARATIVE EXAMPLES 6–8

By using L-valyl-glycyl-L-valyl-L-alanyl-L-propylglycine (Val-Gly-Val-Ala-Pro-Gly) (produced by Sigma) as the substrate, amidation reaction was carried out. The sera were prepared in the same manner as in Examples 4 and 5 from the bloods of horse, porcine, bovine and rabbit. Also, adrenocoriticotropic hormone (ACTH) secreting mouse culture cell At T-20 extract was also compared as the amidation enzymatic solution. At T-20 cells were cultured according to the culturing method as described in the strain Catalogue I of American Type Culture Collection (ATCC) (15th Edition, 1982), from the cells which had become confluent, and the extract was obtained according to the method of Hains et al (Hains et al, Endocrinology, 14, 1522, 1984).

The amidatation enzymatic reactions were carried out in mixtures at concentrations as described in Examples 4, 5, Comparative Examples 1 to 5. However, the substrate concentration was made 25 $\mu$M, and the total volume made 0.5 ml and 300 $\mu$l of the amidation enzymatic mixture was used. The reaction product was detected by HPLC. As the elution solvent, 1 mM ammonium carbonate (pH 9.0) and acetonitrile were used, and a linear concentration gradient was applied which increased acetonitrile from 0% to 60% in 40 minutes. The polypeptide was detected by absorption at 214 nm. The retention time of the unreacted Val-Gly-Val-Ala-Pro-Gly was 9.7 minutes. The amidated reaction product lost charges at C-terminal under the condition of pH 9 to become hydrophobic, whereby the retention time became longer, and it was detected after 13.5 minutes. The reaction mixture was eluted under this condition, and substrate conversion and recovery were determined from the peak area (C) at 9.7 minutes and the peak area (D) at 13.5 minutes.

$$\text{Substrate conversion (\%)} = \frac{D}{C + D} \times 100$$

$$\text{Recovery (\%)} = \frac{C + D}{\text{Peak area at 9.7 min. of unreacted solution}} \times 100$$

The results are summarized in Table 3. The results of the reaction are those after 5 hours.

TABLE 3

Amidation reaction of Val—Glv—Val—Ala—Pro—Gly

| | Amidation enzyme solution | Recovery (%) | Substrate conversion (%) |
|---|---|---|---|
| Example 6 | Horse serum | 85 | 82 |
| Example 7 | Porcine serum | 82 | 71 |
| Comparative Example 6 | Bovine serum | 16 | 50 |
| Comparative Example 7 | Rabbit serum | 67 | 11 |
| Comparative Example 8 | A + T20 extract | 0 | unmeasurable |

Even when the substrate is Val-Gly-Val-Ala-Pro-Gly, the horse serum and the porcine serum exhibited a higher substrate conversion and recovery compared with other enzyme solutions. In At T-20 extract, substantially no polypeptide could be recovered. It may be considered that it was decomposed with intrinsic protease.

EXAMPLES 8–11 COMPARATIVE EXAMPLES 9–12

By use of glycyl-L-phenylalanyl-glycine (Gly-Phe-Gly) (produced by Kokusan Kagaku), L-leucine-glycyl-glycine (Leu-Gly-Gly) (produced by Kokusan Kagaku) as the substrate, amidation reaction was carried out. As Comparative Examples, examples using glycyl-glycyl-L-leucine (Gly-Gly-Leu) (produced by Kokusan Kagaku) and L-tyrosyl-L-tyrosyl-L-tyrosine (Tyr-Tyr-Tyr) (produced by Kokusan Kagaku) as the substrate are shown.

The horse and porcine sera used were the same as those used in Examples 4 and 5.

The amidation enzymatic reaction conditions and the detection conditions of the polypeptide formed were conducted according to the conditions as shown in Examples 6 and 7. The amidation reaction efficiencies obtained from the peaks detected by HPLC are summarized in Table 4. The results of the reactions were for those of 30° C. and 18 hours.

TABLE 4

Amidation of peptide with horse and porcine serum

| | Serum | Substrate | Unreacted substrate retention time (min) | Product retention time (min) | Recovery (%) | Substrate conversion (%) |
|---|---|---|---|---|---|---|
| Example 8 | Horse | Gly—Phe— | 8.2 | 11.8 | 86 | 87 |
| Example 9 | Porcine | Gly | | | 79 | 80 |
| Example 10 | Horse | Leu—Gly— | 6.7 | 10.4 | 94 | 71 |
| Example 11 | Porcine | Gly | | | 91 | 82 |
| Comparative Example 9 | Horse | Gly—Gly—Leu | 8.9 | Not detected | 103 | 0 |
| Comparative Example 10 | Porcine | | | | 91 | 0 |
| Comparative Example 11 | horse | Tyr—Tyr—Tyr | 2.5 | Not detected | 98 | 0 |
| Comparative Example 12 | Porcine | | | | 89 | 0 |

Both horse serum and porcine serum suitably amidated the C-terminal of Gly-Phe-Gly, Leu-Gly-Gly. In contrast, Gly-Gly-Leu, Tyr-Tyr-Tyr could not be amidated. Thus, the reaction proved to be specific for C-terminal glycine.

The amidated peptide which is the reaction product could be easily purified by separation through HPLC. By blowing nitrogen into the separated solution to evaporate acetonitrile, followed further by lyophilization, ammonium carbonate was sublimated and pure products of glycyl-L-phenylalanineamide and L-leucyl-glycineamide of the products could be obtained.

EXAMPLES 12 and 13

Amidation of human calcitonin glycine adduct was conducted. According to the method as described in Japanese Patent Application No. 62-60171 (filed on Mar. 17, 1987, Novel Gene, its Expression Plasmid DNA and Transformed Microorganism, Applicant: Kabushiki Kaisha Shiseido), human calcitonin precursor having glycine peptide bonded to L-proline reside at C-terminal of human calcitonin was prepared and purified by separation.

Partial purification of horse serum and porcine serum was carried out as described below. Two ml of serum was filtered through Millipore filter 30,000 cut-off (produced by Nippon Millipore Limited) and the fractions with molecular weights of 30,000 containing the amidation enzyme protein were concentrated to 1 ml. This was washed with 1 ml of Tris-HCl buffer pH 7.0, and used as the partially purified product. By this operation, the yield of the amidation enzyme in the horse serum was 82%, with the specific activity being elevated from 28 to 62 (pmol/hr/mg). Also, concerning porcine serum, the yield was 78%, with the specific activity being elevated from 21 to 45 (pmol/hr/mg).

The amidation reaction conditions were according to the conditions as shown in Examples 6, 7, and the reaction volume was made 1 ml. The human calcitonin glycine adduct which is the substrate was used in an amount of 10 μg. The purified serum solution was used in an amount of 500 μl. The separation results of the product by HPLC are shown in Table 5.

TABLE 5

| | Serum purified fraction | Substrate retention time (min.) | Product retention time (min.) | Recovery (%) | Substrate conversion (%) |
|---|---|---|---|---|---|
| Example 9 | Horse | 18.8 | 23.1 | 67 | 61 |
| Example 10 | Porcine | | | 74 | 53 |

Also by using human calcitonin glycine adduct with 33 amino acid residues as the substrate, the amidation reaction was suitably carried out.

The human calcitonin produced was recovered according to the method shown in Examples 8 to 11, and lyophilized. The human calcitonin powder obtained can be used as a pharmaceutical.

Industrial Applicability

The enzyme composition of the present invention can be used in the production of a compound represented by the formula (II) from a compound represented by the formula (I) according to an enzymatic reaction and an enzyme active reagent for study in the art, and the process for preparing the enzyme composition may be useful for the production thereof, and serum or plasma of horse or porcine can be used in production of the above compound.

I claim:

1. A C-terminal amidating enzyme composition derived from porcine or equine serum or plasma which comprises a C-terminal amidating enzyme capable of amidating a C-terminal glycine adduct, wherein said amidating enzyme (i) amidates the carboxy terminus of the C-terminal glycine of a peptide selected from the group consisting of D-Tyr-Val-Gly, D-Tyr-Trp-Gly, Gly-Phe-Gly, Phe-Gly-Phe-Gly, D-Tyr-Leu-Asn-Gly, Arg-Phe-Gly, Arg-Ala-Arg-Leu-Gly, Leu-Met- Gly, Gly-Leu-Met-Gly, Phe-Gly-Leu-Met-Gly, Asp-Arg-Phe-Gly, Trp-Asp-Arg-Phe-Gly, Ala-Phe-Gly, Lys-Ala-Phe-Gly, Ser-Lys-Ala-Phe-Gly, Arg-Tyr-Gly, Gly-Met-Gly, Gly-Tyr-Gly, Gly-His-Gly, His-Gly-Gly, and Trp-Gly-Gly;

(ii) is stable in the pH range of 5 to 9;
(iii) has as cofactors metal ions and L-ascorbic acid;
(iv) has two active fractions at molecular weights of about 50,000 and about 100,000 as determined from gel filtration;
(v) has isoelectric points of about 4.5 pH for the active fraction having a molecular weight of about 50,000 and about 6.7 pH for the active fraction having a molecular weight of about 100,000 according to isoelectric point chromatography; and
(vi) is activated by addition of catalase.

2. A composition according to claim 1 which further comprises $Cu^{2+}$.

3. A composition according to claim 1 wherein the C-terminal amidating enzyme comprises the active fraction having a molecular weight of about 50,000 as determined from gel filtration.

4. A composition according to claim 1 wherein the C-terminal amidating enzyme comprises the active fraction having a molecular weight of about 100,000 as determined from gel filtration.

5. A process for preparing a C-terminal amidating enzyme composition according to claim 1, which comprises
subjecting porcine or equine serum or plasma to substrate affinity chromatography, wherein the substrate is a peptide selected from the group consisting of D-Tyr-Val-Gly, D-Tyr-Trp-Gly, Gly-Phe-Gly, Phe-Gly-Phe-Gly, D-Tyr-Leu-Asn-Gly, Arg-Phe-Gly, Arg-Ala-Arg-Leu-Gly, Leu-Met-Gly, Gly-Leu-Met-Gly, Phe-Gly-Leu-Met-Gly, Asp-Arg-Phe-Gly, Trp-Asp-Arg-Phe-Gly, Ala-Phe-Gly, Lys-Ala-Phe-Gly, Ser-Lys-Ala-Phe-Gly, Arg-Tyr-Gly, Gly-Met-Gly, Gly-Tyr-Gly, Gly-His-Gly, His-Gly-Gly, and Trp-Gly-Gly, and
eluting with a butter solution having a pH of between 7.0 and 9.0 and containing about 1 to 40% acetonitrile and 0.1 to 1M sodium chloride.

6. A method of producing a C-terminal amidated compound, which comprises
treating a C-terminal glycine adduct with a composition according to claim 1 in the presence of about 1 to 10% by volume of acetonitrile based on total volume of the composition.

* * * * *